United States Patent
Cuff et al.

(10) Patent No.: US 6,713,494 B1
(45) Date of Patent: Mar. 30, 2004

(54) AMORPHOUS BENZOTHIOPHENES, METHODS OF PREPARATION AND METHODS OF USE

(75) Inventors: George William Cuff, Carmel, IN (US); Arvind Lavji Thakkar, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 938 days.

(21) Appl. No.: 08/918,741

(22) Filed: Aug. 25, 1997

Related U.S. Application Data (60) Provisional application No. 60/024,831, filed on Aug. 28, 1996.

(51) Int. Cl.[7] ............... A61K 31/445; C07D 409/10
(52) U.S. Cl. ............................................. 514/324
(58) Field of Search ................ 540/596; 546/202; 568/525; 514/324, 442, 443, 146

(56) References Cited

U.S. PATENT DOCUMENTS

| | | | |
|---|---|---|---|
| 3,394,125 A | 7/1968 | Crenshaw | 548/525 |
| 3,413,305 A | 11/1968 | Crenshaw | 548/525 |
| 4,133,814 A | 1/1979 | Jones et al. | 546/202 |
| 4,230,862 A | 10/1980 | Suarez et al. | 546/237 |
| 4,358,593 A | 11/1982 | Jones et al. | 546/202 |
| 4,380,635 A | 4/1983 | Peters | 546/202 |
| 4,418,068 A | 11/1983 | Jones et al. | 546/237 |
| 5,395,842 A | 3/1995 | Labrie | 514/320 |
| 5,470,854 A | 11/1995 | Angerer et al. | 514/233 |
| 5,472,962 A | 12/1995 | Koizumi et al. | 514/324 |
| 5,672,612 A | * 9/1997 | Ronsen et al. | 514/338 |

FOREIGN PATENT DOCUMENTS

| | | |
|---|---|---|
| EP | 062 503 | 10/1982 |
| WO | WO 89/0289 | 4/1989 |
| WO | WO 95/10513 | 4/1995 |

OTHER PUBLICATIONS

Eagleson "Concise encyclopedia Chemistry" Water de Gruyter, 1993.*
Ulicky et al. "Comprehensive dictionay of physicao chemistry" PTR prentice hall, 1990.*
Yasuhiko et al. "Characterization of amorphous ursodeocycholic acid prepared by spray–drying technique" JICST 03282368, 1992.*
Matsuda et al. "Amorphism and physicochemical stability of spray–dried frusemide" Medline 93058373, 1992.*
Uekama et al. "Inhibitory effect of 2=hydroxypropyl–beta––cyclodextrin on crystal–growth of nefedipine . . . " Medline 92333423, 1993.*
Yano et al. "Crystal forms, improvements of dissolution and absorption of poorly water–soluble . . . " Medline 96428160, 1996.*
Evans "An introduction to crystal chemistry" Cambridge Press, p. 393–397, 1964.*
Hannay "Treatise on solid state chemistry" Plenum Press, p. 89–90, 1977.*
Takeuchi et al. "Progress of powder technology. Particle design and manufacturing" chem. Engineer. v.37, p. 496–501, 1992.*
Kai et al. "Oral absorption improvement of poorly soluble drug using solid dispersion technique" chem. Pharm. Bull. v. 44(3)568–571, 1996.*
Lieberman et al. "Pharmaceutical dosage forms" Marcel Dekker, Inc. p. 462–465, 1989.*
Crenshaw, R.R., et al, *J. Med. Chem.* 14 (12):1185–1190 (1971).
Jones, C.D., et al, *J. Med. Chem.* 27:1057–1066) 1984.
Jones, C.D., et al, *J. Med. Chem.* 35: 931–938 1992.

* cited by examiner

*Primary Examiner*—Ceila Chang
(74) *Attorney, Agent, or Firm*—Gary M. Birch; Gilbert T. Voy

(57) ABSTRACT

The instant invention provides an amorphous form of a compound of formula I

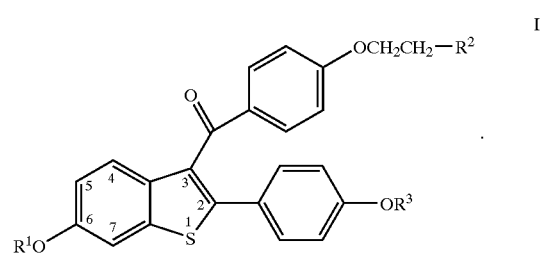

Methods of preparing an amorphous form of a compound of formula I, pharmaceutical formulations containing same, and methods of using same are also provided.

10 Claims, 1 Drawing Sheet

FIG. 1

Mean Raloxifene Levels in Plasma from Dogs Dosed With Raloxifene at 4 mg/Kg in Crystalline or Amorphous Form

AMORPHOUS BENZOTHIOPHENES, METHODS OF PREPARATION AND METHODS OF USE

This application claims the benefit of U.S. Provisional Application No. 60/024,831, which was filed on Aug. 28, 1996.

BACKGROUND OF THE INVENTION

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fracturers in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular:disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally,liestrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side, effects and risks associated with estrogen therapy.

A number of structurally unrelated compounds are capable of interacting with the estrogen receptor and producing unique in vivo profiles. Compounds with in vivo profiles typical of a "pure" antagonist (for example, ICI 164,384) or of a relatively "pure" agonist (for example, 17β-estradiol) represent opposite ends of a spectrum in this classification. Between these two extremes lie the SERMs ("selective estrogen receptor modulator"), characterized by clinical and/or preclinical selectivity as full or partial agonists in certain desired tissues (for example, bone), and antagonists or minimal agonists in reproductive tissues. Within this pharmacologic class, individual SERMs may be further differentiated based on profiles of activity in reproductive tissues. Raloxifene, a second generation SERM, displays potentially useful selectivity in uterine tissue with apparent advantages over triphenylethylene-based estrogen receptor ligands. As such, raloxifene appears to be well-suited at least for the treatment of postmenopausal complications, including osteoporosis and cardiovascular disease. It is anticipated that, as further advances are made in the pharmacology and molecular biology of estrogen receptor active agents, further subclassifications of SERMs may evolve in the future along with an increased understanding of the therapeutic utility of these novel classes of estrogenic compounds.

The advancement of raloxifene, in particular, has been somewhat hampered by its physical characteristics, both as to bioavailability and manufacturing. For example, raloxifene is generally insoluble, which may affect bioavailability. Clearly, any improvement in the physical characteristics of raloxifene and in closely related compounds would potentially offer a more beneficial therapy and enhanced manufacturing capabilities.

Thus, it would be a significant contribution to the art to provide amorphous forms of raloxifene and related compounds which have increased solubility, methods of preparation, pharmaceutical formulations, and methods of use.

SUMMARY OF THE INVENTION

The present invention provides a compound of formula I wherein:

R$^1$ and R$^3$ are independently hydrogen, —CH$_3$, —CO (C$_1$–C$_6$ alkyl), or —COAr, wherein Ar is optionally substituted phenyl;

R$^2$ is selected from the group consisting of pyrrolidinyl, hexamethyleneimino, and piperidinyl; or a pharmaceutically acceptable salt or solvate thereof, in an amorphous form.

DETAILED DESCRIPTION

The present invention further provides pharmaceutical formulations containing a compound of formula I.

Still further provided;by way of the instant invention are processes for the preparation of amorphous forms of compounds of formula I.

The instant invention also provides methods of use for the compounds of formula I, including the inhibition of bone loss or bone resorption.

General terms used in the description of compounds herein described bear their usual meanings. For example, the term "C$_1$–C$_6$ alkyl" represents a straight or branched alkyl chain having from 1 to 6 carbon atoms. Typical C$_1$–C$_6$ alkyl groups include methyl, ethyl, n-propyl, and n-butyl. The term "C$_1$–C$_4$ alkoxy" represents groups such as methoxy, ethoxy, n-propoxy, and n-butoxy.

Optionally substituted phenyl includes phenyl and phenyl substituted with C$_1$–C$_6$ alkyl, C$_1$–C$_4$ alkoxy, hydroxy, nitro, chloro, fluoro, or tri(chloro or fluoro)methyl, and the like.

The term "inhibit" includes its generally accepted meaning which includes prohibiting, preventing, restraining, and slowing, stopping, or reversing progression, severity, or ameliorating a resultant symptom or effect.

Preferred embodiments of the current invention are compounds of formula I which include compounds wherein R$^1$ and R$^3$ are hydrogen, and R$^2$ is pyrrolidinyl, piperidinyl, or a hexamethyleneimino group. Representative compounds from this preferred group include:

6-hydroxy-2-(4-hydroxyphenyl)-3-[4-(2-pyrrolidinylethoxy)benzoyl]benzo[b]-thiophene, 6-hydroxy-2-(4-hydroxyphenyl)-3-[4-(2-piperidinylethoxy]benzoyl]benzo[b]thiophene, and 6-hydroxy-2-(4-hydroxy-phenyl)-3-[4-(2-hexamethyleneiminoethoxy)benzoyl]benzo[b]-thiophene.

More preferably, the product of the present invention is the Formula I compounds wherein R$^2$ is a piperidinyl group.

A representative compound from this more preferred group includes: 6-hydroxy-2-(4-hydroxyphenyl)-3-[4-(2-piperidinylethoxy)benzoyl]benzo[b]thiophene.

The compounds of the current invention may be made according to established procedures, such as those detailed in U.S. Pat. Nos. 4,133,814, 4,418,068, and 4,380,635, and European Patent Application 95306050.6, Publication No. 0699672, Kjell, et al., filed Aug. 30, 1995, published Mar. 6, 1996, all of which are herein incorporated by reference. In addition, the information disclosed in the published European Patent Application number 0670162 A1, published on Sep. 6, 1995, is herein incorporated by reference. A crystalline form of raloxifene hydrochloride may be prepared by the methods disclosed in the Example section, infra.

The term "amorphous" includes a physical state which may be verified by x-ray diffraction and other means including but not limited to observation with a polarized light microscope and differential scanning calorimetry.

In general, the process starts with a benzo[b]thiophene having a 6-hydroxyl group and a 2-(4-hydroxyphenyl) group. The starting compound is protected, acylated, and deprotected to form the compounds of formula I. Further examples of the preparation of such compounds are also provided in the references discussed above.

The compound of formula I according to the present invention is conveniently prepared by a process which constitutes a further feature of the present invention, and which comprises recovering a compound of formula I from a solution thereof under conditions whereby an amorphous product is obtained.

The amorphous material of the instant invention was prepared by dissolving a crystalline form of a compound of formula I in a suitable solvent or solvent mixture, such as, for example, methanol and water, followed by recovery of the material by any suitable means. Techniques which may be employed to recover amorphous compounds of formula I from the solution include those wherein the solvent is removed from the solution, preferably rapidly, and the product deposited, and those wherein the product is precipitated from a solution. Methods involving the use of these procedures which have been found to be satisfactory include spray drying, roller drying, solvent precipitation, rotary evaporation, and freeze drying. Particularly preferred for the practice of the present invention is the method of spray drying.

Solvents which may be employed in the practice of the present invention will be chosen according to the technique and conditions to be employed, and include water, methanol, ethanol, and the like, including mixtures thereof, if desired.

The concentration of a:.compound of formula I in the solvent is advantageously as high as possible, commensurate with an amorphous form of a compound of formula I being obtained, with preferrable concentrations being in the range of from about 5 mg/ml to about 40 mg/ml. The higher concentrations obtained will typically depend on the solvent system employed in the preparation, and/or the presence or absence of povidone (PVP) or hydroxypropyl-β-cyclodextrin (HPBCD). The solvents may, if desired, be heated as an aid to solubility and solvent removal.

In general, the compounds of formula I have sufficient heat stability to withstand spray drying and the like, and accordingly, spray drying is the preferred method of recovery. Spray drying systems may be operated in a known manner to obtain an amorphous product essentially free from crystalline material as well as free from particulate contaminants. Closed cycle spray drying systems in which the drying medium is recycled are particularly safe and economic for use in obtaining the product of the present invention.

The drying gas employed in the process may be air, but preferred for the use with flammable solvents are inert gases such as, for example, nitrogen, argon and carbon dioxide. Preferred would be nitrogen. The gas inlet temperature to the spray dryer is chosen according to the solvent employed, but would be, for example, in the range of from about 75° C. to about 150° C.

The presence of the amorphous form of a compound of formula I was determined by observing the material under a polarized light microscope, and determining if the material was birefringent. If no birefringence was observed, the material was considered to be amorphous.

A compound of formula I in accordance with the present invention is preferably essentially free from the crystalline form of the material. Long term studies have indicated the amorphous form of the instant invention is very stable. However, once recovered as amorphous material, conversion to the crystalline form may be prevented by the addition of any number of stabilizer materials known in the art, such as, for example, povidone, hydroxypropyl methylcellulose (HPMC), hydroxypropylcellulose (HPC), polyethylene glycol (PEG), hydroxypropyl-β-cyclodextrin (HPB), cyclodextrin, and the like.

Solubility of the amorphous form was demonstrated to be approximately 250 times greater than the crystalline form. Advantages of increased solubility include but are not limited to ease in processing the amorphous material, which includes equipment cleaning issues; ease in formulation and delivery of the material, and the like.

A compound of formula I in an amorphous form may also be combined with a number of other materials prior to or after spray drying, or otherwise processed to provide amorphous material, which may in turn be further formulated for processing.

Compounds of formula I which are amorphous have been demonstrated to have several advantages, including but not limited to a high degree of bioavailability, as well as being in a form for effective methods of administration.

The term "solvate" represents an aggregate that comprises one or more molecules of the solute, such as a formula I compound, with one or more molecules of solvent. Although the free-base form of formula I compounds can be used in the methods of the present invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The present invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the present invention which is capable of inhibiting, alleviating, ameliorating, treating, or preventing further symptoms in mammals, including humans, suffering from estrogen deprivation, for example, menopause or ovariectomy, or inappropriate estrogen stimulation such as uterine fibrosis or endometriosis, or suffering from aortal smooth muscle cell profileration or restenosis. In the case of estrogen-dependent cancers, the term "effective amount" means the amount of compound of the present invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar agar, calcium carbonate, and sodium bicarbonate; agents for retarding dissollution such as paraffin; resorption accelerators such as quaternary ammonium compounds; surfacelactive agents such as cetyl alcohol, glycerol monostearate; adsorptive carriers such as kaolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage:of a compound of formula I required to treat, inhibit, or prevent the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg. Such dosages will be administered to a patient in need of treatment from one to three times each day or as often as needed for efficacy, and for periods of at least two months, more typically for at least six months, or chronically.

As a further embodiment of the invention, the compounds of formula I may be administered along with an effective amount of an additional therapeutic agent, including but not limited to estrogen, progestin, benzothiophene compounds having including raloxifene, naphthyl compounds having antiestrogen activity, bisphosphonate compounds such as alendronate and tiludronate, parathyroid hormone (PTH), including truncated and/or recombinant forms of PTH such as, for example, PTH (1–34), calcitonin, bone morphogenic proteins (BMPs), or combinations thereof. The different forms of these additional therapeutic agents available as well as the various utilities associated with same and the applicable dosing regimens are well known to those of skill in the art.

Various forms of estrogen and progestin are commercially available As ;used herein, the term "estrogen" includes compounds having estrogen activity and estrogen-based agents. Estrogen compounds useful in the practice of the present invention include, for example, estradiol estrone, estriol, equilin, equilenin, estradiol cypionate, estradiol valerate, ethynyl estradiol, polyestradiol phosphate, estropipate, diethylstibestrol, dienestrol, chlorotrianisene, and mixtures thereof. Estrogen-based agents, include, for example, 17-α-ethynyl estradiol (0.01–0.03 mg/day), mestranol (05–0.15 mg/day), and conjugated estrogenic hormones such as Premarin® (Wyeth-Ayerst; 0.2–2.5 mg/day). As used herein, the term "progestin" includes compounds having progestational activity such as, for example, progesterone, norethynodrel, norgestrel, megestrol acetate, norethindrone, progestin-based agents, and the like. Progestin-based agents include, for example, medroxyprogesterone such as Provera® (Upjohn; 2.5–10 mg/day), norethylnodrel (1.0–10.0 mg/day), and norethindrone (0.5–2.0 mg/day). A preferred estrogen-based compound is Premarin®, and norethylnodrel and norethindrone are preferred progestin-based agents. The method of administration of each estrogen- and progestin-based agent is consistent with that known in the art.

The formulations which follow are given for purposes of illustration and are not intended to be limiting in any way. The total active ingredients in such formulations comprises from 0.1% to 99.9% by weight of the formulation. The term "active ingredient" means a compound of formula I.

| Formulation 1: Gelatin Capsules | |
|---|---|
| Ingredient | Quantity (mg/capsule) |
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

| Formulation 2: Tablets | |
|---|---|
| Ingredient | Quantity (mg/tablet) |
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

| Formulation 3: Suppositories | |
|---|---|
| Ingredient | Weight |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

The following examples and preparations are provided to better elucidate the practice of the present invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

EXAMPLES

NMR data for the following Examples were generated on a GE 300 MHz NMR instrument, and anhydrous d-6 DMSO was used as the solvent unless otherwise indicated.

All experiments were run under positive pressure of dry nitrogen. All solvents and reagents were used as obtained.

The percentages are generally calculated on a weight (w/w) basis; except for HPLC solvents which are calculated on a volume (v/v) basis. Proton nuclear magnetic resonance ($^1$H NMR) spectra were obtained on a Bruker AC-300 FTNMR spectrometer at 300.135 MHz. Melting points were determined by differential scanning calorimetry (DSC) in a TA Instrument DCS 2920 using a closed cell and a heating rate of 2° C./minute. The reactions were generally monitored for completion using high performance liquid chromatography (HPLC). The X-ray powder diffraction spectra were obtained in a Siemens D5000 X-Ray Powder Diffraktometer, using copper radiation and a Si(Li) detector. Some reactions were monitored using a Zorbax Rx-C8 column, (25 cm×4.6 mm ID, 5μ particle) eluting with a mixture of 60 mM phosphate ($KH_2PO_4$) and 10 mM octanesulfonate (pH 2.0)/acetonitrile (60:40).

The acylation, dealkylation, or acylation/dealkylation reactions are also monitored for completion by HPLC. A sample of the reaction mixture was assayed using a Zorbax Rx-C8 column, (25 cm×4.6 mm ID, 5μ particle), eluting with a gradient as shown below:

GRADIENT SOLVENT SYSTEM

| Time (min.) | A (%) | B (%) |
|---|---|---|
| 0 | 60 | 40 |
| 5 | 60 | 40 |
| 10 | 45 | 55 |
| 20 | 38 | 62 |
| 25 | 45 | 55 |
| 32 | 45 | 55 |
| 37 | 60 | 40 |
| 42 | 60 | 40 |

A: 0.05 M $HClO_4$ (pH = 2.0)
B: acetonitrile

The reaction mixture was analyzed by diluting a 0.1 to 0.2 mL sample to 50 mL with a 60:40 mixture of A/B. Similarly, the mother liquor of the recrystallizations was sampled in a similar manner.

The amount (percentages) of 6-hydroxy-2-(4-hydroxyphenyl)-3-[4-(2-piperidinylethoxy)benzoyl]benzo[b]thiophene hydrochloride in the crystalline material (potency) was determined by the following method. A sample of the crystalline solid (5 mg) was weighed into a 100-mL volumetric flask, and dissolved in a 70/30 (v/v) mixture of 75 mM potassium phosphate buffer (pH 2.0) and acetonitrile. An aliquot of this solution (10 μL) was assayed by high performance liquid chromatography, using a Zorbax Rx-C8 column (25 cm×4.6 mm ID, 5μ particle) and UV detection (280 nm). The following gradient solvent system is used:

Gradient Solvent System (Potency)

| time (min) | A (%) | B (%) |
|---|---|---|
| 0 | 70 | 30 |
| 12 | 70 | 30 |
| 14 | 25 | 75 |
| 16 | 70 | 30 |
| 25 | 70 | 30 |

A: 75 mM $KH_2PO_4$ buffer (pH 2.0)
B: acetonitrile

The percentage of 6-hydroxy-2-(4-hydroxyphenyl)-3-[4-(2-piperidinylethoxy)benzoyl]benzo[b]thiophene hydrochloride in the sample is calculated using the peak area, slope (m), and intercept (b) of the calibration curve with the following equation:

$$\% \text{ potency} = \frac{\text{peak area} - b}{m} \times \frac{\text{sample volume (mL)}}{\text{sample weight (mg)}}$$

The amount (percentage) of solvent, such as methanol, ethanol, or 1,2-dichloroethane, present in the crystalline material is determined by gas chromatography. A sample of the crystalline solid (50 mg) was weighed into a 10-mL volumetric flask, and dissolved in a solution of 2-butanol (0.025 mg/mL) in dimethylsulfoxide. A sample of this solution was analyzed on a gas chromatograph using a DB Wax column (30 m×0.53 mm ID, 1μ particle), with a column flow of 10 mL/min and flame ionization detection. The column temperature was heated from 35° C. to 230° C. over a 12 minute period. The amount of solvent was determined by comparison to the internal standard (2-butanol), using the following formula:

$$\% \text{ solvent} = \frac{C}{D} \times \frac{E}{F} \times \frac{G}{H} \times I$$

wherein:
C=ratio of solvent in sample
D=average ratio of standard for specific solvent
E=average weight of standard
F=weight of sample (mg)
G=volume of sample (10 mL)
H=volume of standard (10,000 mL)
I=purity of standard (%)

Preparation 1

6-Methoxy-2-(4-methoxyphenyl)benzo[b]thiophene

A solution of 3-methoxybenzenethiol (100 grams) and potassium hydroxide (39.1 grams) in water (300 mL) was added to denatured ethanol (750 mL), and the resulting mixture cooled to about 0° C. The cold mixture was treated with 4'-methoxyphenacyl bromide (164 grams) in several small portions. Upon complete addition, the mixture was cooled for an additional ten minutes, then allowed to warm to room temperature. After three hours, the mixture was concentrated in vacuo, and the residue treated with water (200 mL). The resulting mixture was treated with ethyl acetate, and the phases were separated. The organic phase was washed with water (2×), sodium bicarbonate solution (2×), and sodium chloride solution (2×). The organic phase was then dried over magnesium sulfate, filtered, and evaporated to dryness in vacuo to give 202 grams of α-(3-methoxyphenylthio)-4-methoxyacetophenone. This crude product was crystallized from methanol and washed with hexane to give 158 grams. Melting point 53° C.

Polyphosphoric acid (930 grams) was heated to 85° C. and treated with the intermediate product from above (124 grams) in small portions over 30 minutes. Upon complete addition, the resulting mixture was stirred at 90° C. After an additional 45 minutes, the reaction mixture was allowed to cool to room temperature. This mixture was treated with crushed ice while the mixture was cooled in an ice bath. The resulting mixture was treated with water (100 mL) producing a light pink precipitate. The precipitate was isolated by filtration, washed with water and methanol, and dried in vacuo at 40° C. to give 119 grams of 6-methoxy-2-(4-methoxyphenyl)benzo[b]thiophene. This crude product was slurried in hot methanol, filtered, and washed with cold methanol. The resulting solid material was recrystallized from ethyl acetate (4 liters), filtered, washed with hexane, and dried in vacuo to 68 grams of the title compound. Melting point 187–190.5° C.

Preparation 2

Ethyl 4-(2-Piperidinylethoxy)benzoate

A mixture of ethyl 4-hydroxybenzoate (8.31 g), 1-(2-chloroethyl)piperidine monohydrochloride (10.13 g), potassium carbonate (16.59 g), and methyl ethyl ketone (60 mL) was heated to 80° C. After one hour, the mixture was cooled to about 55° C. and treated with additional 1-(2-chloroethyl) piperidine mono-hydrochloride (0.92 g). The resulting mixture was heated to 80° C. The reaction was monitored by thin layer chromatography (TLC), using silica-gel plates and ethyl acetate/acetonitrile/triethylamine (10:6:1, v/v). Additional portions of 1-(2-chloroethyl)piperidine hydrochloride are added until the starting 4-hydroxybenzoate ester is consumed. Upon complete reaction, the reaction mixture was treated with water (60 mL) and allowed to cool to room temperature. The aqueous layer was discarded and the organic layer concentrated in vacuo at 40° C. and 40 mm Hg. The resulting oil was used in the next step without further purification.

Preparation 3

4-(2-Piperidinylethoxy)benzoic Acid Hydrochloride

A solution of the compound prepared as described in Preparation 2 (about 13.87 g) in methanol (30 mL) was treated with 5 N sodium hydroxide (15 mL), and heated to 40° C. After 4 ½ hours, water (40 mL) was added. The resulting mixture was cooled to 5–10° C., and concentrated hydrochloric acid (18 mL) was added slowly. The title compound crystallized during acidification. This crystalline product was collected by filtration, and dried in vacuo at 40–50° C. to give 83% yield of the title compound. Melting point 270–271° C.

Preparation 4

6-Methoxy-2-(4-methoxyphenyl)-3-[4-(2-piperidinylethoxy)benzoyl]-benzo[b]thiophene Hydrochloride A mixture of the compound prepared as described in Preparation 1 (8.46 grams) and the acid chloride prepared as described in Preparation 3 (10.0 grams) in methylene chloride (350 mL) was cooled:to about 20–25° C. The cool mixture was treated with boron trichloride (2.6 mL), and the resulting mixture mechanically stirred. The reaction was monitored by HPLC using the assay described above. After 85 minutes, the in situ HPLC yield based on a 6-methoxy-2-(4-methoxyphenyl)-3-[4-(2-piperidinylethoxy)benzoyl] benzo[b]thiophene standard was 88%.

Preparation 5

6-Hydroxy-2-(4-hydroxyphenyl)-3-[4-(2-piperidinylethoxy)benzoyl]-benzo[b]thiophene Hydrochloride 1,2-Dichloroethane Solvate (crystal Form I)

A solution of 6-methoxy -2-(4-methoxyphenyl)-3-[4-(2-piperidinylethoxy)benzoyl]benzo[b]thiophene hydrochloride (2.0 g) in 1,2-dichloroethane (20 mL) was treated with boron trichloride (2.0 mL). The resulting mixture was stirred at 35° C. for about 18 hours. A:mixture of ethanol and methanol (10 mL, 95:5, 3A) was treated with the reaction mixture from above, causing the alcoholic mixture to reflux. Upon complete addition, the resulting crystalline slurry was stirred at 25° C. After one 1 hour, the crystalline product was filtered, washed with cold ethanol (10 mL), and dried at 40° C. in vacuo to give 1.78 g of the title compound. The X-ray powder diffraction pattern is identical to that reported in Table 1.

Potency: 80.2%

1,2-Dichloroethane: 7.5% (gas chromatography)

TABLE 1

X-ray Diffraction Pattern for Crystal Form 1.

| d-line spacing (Angstroms) | I/I$_o$ (×100) |
| --- | --- |
| 16.1265 | 3.80 |
| 10.3744 | 8.63 |
| 8.3746 | 5.29 |
| 7.9883 | 36.71 |
| 7.2701 | 5.06 |
| 6.5567 | 70.77 |
| 6.2531 | 6.79 |
| 5.5616 | 24.05 |
| 5.3879 | 100.00 |
| 5.0471 | 89.64 |
| 4.7391 | 85.96 |
| 4.6777 | 39.36 |
| 4.6332 | 62.60 |
| 4.5191 | 77.56 |
| 4.2867 | 36.82 |
| 4.2365 | 41.66 |
| 4.1816 | 49.60 |
| 4.0900 | 11.28 |
| 3.9496 | 11.85 |
| 3.7869 | 36.25 |
| 3.7577 | 56.16 |
| 3.6509 | 40.62 |
| 3.5751 | 15.65 |
| 3.5181 | 21.52 |
| 3.4964 | 18.53 |
| 3.4361 | 33.60 |
| 3.3610 | 6.21 |
| 3.3115 | 4.95 |
| 3.2564 | 7.36 |
| 3.2002 | 3.80 |
| 3.1199 | 15.77 |
| 3.0347 | 14.84 |
| 2.8744 | 9.67 |
| 2.8174 | 10.82 |
| 2.7363 | 11.51 |

The amount of 6-hydroxy-2-(4-hydroxyphenyl)-3-[4-(2-piperidinylethoxy)benzoyl]benzo[b]thiophene hydrochloride present in the crystalline material is about 87.1%, as determined using the high performance liquid chromatography (HPLC) assay described below. The amount of 1,2-dichloroethane present in the crystalline material is about 0.55 molar equivalents, as determined by proton nuclear magnetic resonance spectroscopy.

Preparation 6

6-Hydroxy-2-(4-hydroxyphenyl)-3-[4-(2-piperidinylethoxy)benzoyl]benzo[b]thiophene Hydrochloride 1,2-Dichloroethane Solvate (Crystal Form I)

A mixture of the compound prepared as described in Preparation 2 (15 g) and dimethylformamide (0.2 mL) in 1,2-dichloroethane (250 mL) was cooled to 0° C. Phosgene (8.25 mL) was condensed in a cold, jacketed addition funnel (−10° C.), and added to the cold mixture over a period of two minutes. The resulting mixture was heated to about 47° C. After about two and one half hours, the reaction was assayed by HPLC for completion. Additional phosgene may be added to drive the reaction to completion. Excess phosgene was removed by vacuum distillation at 30–32° C. and 105–110 mm Hg.

After about three to four hours, the reaction solution was treated with the compound prepared as described in Preparation 1 (13.52 g). The resulting solution was cooled to 0° C. Boron trichloride (12.8 mL) was condensed in a graduated cylinder, and added to the cold reaction mixture. After eight hours at 0° C., the reaction solution was treated with additional boron trichloride (12.8 mL). The resulting solution was heated to 30° C. After 15 hours, the reaction was monitored for completion by HPLC.

A mixture of ethanol and methanol (125 mL, 95:5, 3A) was heated to reflux, and treated with the reaction solution from above over a 60 minute period. Upon complete addition, the acylation/demethylation reaction flask was rinsed with additional ethanol (30 mL). The resulting slurry was allowed to cool to room temperature with stirring. After one hour at room temperature, the crystalline product was filtered, washed with ethanol (75 mL), and dried at 40° C. in vacuo to give 25.9 g of the title compound. The X-ray powder diffraction pattern is reported in Table 1. Melting point 261° C.

Potency: 87.1%

1,2-Dichloroethane: 0.55 molar equivalents ($^1$H NMR)

Preparation 7

6-Hydroxy-2-(4-hydroxyphenyl)-3-[4-(2-piperidinylethoxy)benzoyl]-benzo[b]thiophene Hydrochloride Chlorobenzene Solvate (Crystal Form 3)

A solution of the compound prepared as described in Preparation 1 (2.92 grams) and the acid chloride prepared as described in Preparation 4 (3.45 grams) in chlorobenzene (52 mL) was cooled to about 0° C. The cold solution was treated with boron trichloride (2.8 mL). The resulting mixture was mechanically stirred at about 0° C. After three hours, additional boron trichloride (2.8 mL) was added, and the reaction mixture was allowed to warm to room temperature. After about 16–20 hours, the reaction mixture was cooled to 0° C. The cold reaction was quenched by the slow addition of ethanol (26 mL) over 30 minutes. During the addition of the alcohol, a crystalline solid formed. Upon complete addition of the alcohol, the resulting mixture was stirred at room temperature for one hour. The crystalline solid was removed by filtration, washed with cold ethanol (25 mL), and dried in vacuo at 40° C. to give 5.94 grams of the title compound as a yellow solid. The X-ray powder diffraction pattern is identical to that reported in Table 2. Melting point 247° C.

Potency: 78.6%

Chlorobenzene: 12.3% (HPLC)

TABLE 2

X-ray Diffraction Pattern for Crystal Form III.

| d-line spacing (Angstroms) | $I/I_o$ (×100) |
|---|---|
| 14.3518 | 7.24 |
| 10.3335 | 6.17 |
| 8.8305 | 4.29 |
| 7.9475 | 38.16 |
| 6.5904 | 64.25 |
| 6.2848 | 6.52 |
| 5.6048 | 28.06 |
| 5.4107 | 100.00 |
| 5.1544 | 11.26 |
| 5.0493 | 53.26 |
| 5.0224 | 46.11 |
| 4.8330 | 76.94 |
| 4.7694 | 34.23 |
| 4.6461 | 50.22 |
| 4.5754 | 38.61 |
| 4.4953 | 72.65 |
| 4.3531 | 49.15 |
| 4.2940 | 41.64 |
| 4.2425 | 35.75 |
| 4.1856 | 21.63 |
| 4.1338 | 9.47 |
| 4.0793 | 12.69 |
| 3.9960 | 18.50 |
| 3.9037 | 9.03 |
| 3.7854 | 40.39 |
| 3.7521 | 54.16 |
| 3.6787 | 28.60 |
| 3.6509 | 17.96 |
| 3.5444 | 31.72 |
| 3.4679 | 41.55 |
| 3.3899 | 7.69 |
| 3.3101 | 5.72 |
| 3.2561 | 7.42 |
| 3.1784 | 15.19 |
| 3.0445 | 11.17 |
| 3.0146 | 8.94 |
| 2.9160 | 11.89 |
| 2.8217 | 18.23 |
| 2.7500 | 12.06 |
| 2.6436 | 9.65 |
| 2.6156 | 6.97 |

The amount of 6-hydroxy-2-(4-hydroxyphenyl)-3-[4-(2-piperidinylethoxy)benzoyl]benzo[b]thiophene hydrochloride present in the crystalline material is about 78.6%. The amount of chlorobenzene present in the crystalline material is about 12.3%, as determined by HPLC.

Preparation 8

6-Hydroxy-2-(4-hydroxyphenyl)-3-[4-(2-piperidinylethoxy)-benzoyl]benzo[b]thiophene Hydrochloride A solution of sodium hydroxide (0.313 g) in methanol (10 mL) was diluted with additional methanol (40 mL) and water (10 mL). This solution was treated with the compound prepared as described in Example 5 (4.0 g). The resulting solution was extracted with hexane (2×50 mL) to remove the chlorobenzene. The methanolic phase was treated with 2 N hydrochloric acid (4 mL), producing a crystalline slurry. After one hour, the crystalline product was filtered, washed with methanol (5 mL), and dried at 600 in vacuo to give 2.23 g of the title compound. The X-ray powder diffraction pattern was identical to that reported in Table 3.

TABLE 3

X-ray Diffraction Pattern for Non-solvated Crystal Form.

| d-line spacing (Angstroms) | I/I$_o$ (×100) |
|---|---|
| 13.3864 | 71.31 |
| 9.3598 | 33.16 |
| 8.4625 | 2.08 |
| 7.3888 | 7.57 |
| 6.9907 | 5.80 |
| 6.6346 | 51.04 |
| 6.1717 | 29.57 |
| 5.9975 | 5.67 |
| 5.9135 | 9.87 |
| 5.6467 | 38.47 |
| 5.4773 | 10.54 |
| 5.2994 | 4.74 |
| 4.8680 | 4.03 |
| 4.7910 | 5.98 |
| 4.6614 | 57.50 |
| 4.5052 | 5.75 |
| 4.3701 | 9.03 |
| 4.2516 | 69.99 |
| 4.2059 | 57.64 |
| 4.1740 | 65.07 |
| 4.0819 | 12.44 |
| 3.9673 | 22.53 |
| 3.9318 | 100.00 |
| 3.8775 | 9.07 |
| 3.7096 | 33.38 |
| 3.6561 | 21.65 |
| 3.5576 | 3.36 |
| 3.5037 | 7.97 |
| 3.4522 | 18.02 |
| 3.4138 | 4.65 |
| 3.2738 | 10.23 |
| 3.1857 | 8.90 |
| 3.1333 | 6.24 |
| 3.0831 | 9.43 |
| 3.0025 | 12.13 |
| 2.9437 | 4.96 |
| 2.8642 | 7.70 |
| 2.7904 | 11.95 |
| 2.7246 | 3.05 |
| 2.6652 | 3.32 |
| 2.5882 | 7.30 |

The amount of 6-hydroxy-2-(4-hydroxyphenyl)-3-[4-(2-piperidinylethoxy)benzoyl]benzo[b]thiophene hydrochloride present in the crystalline material is at least 95%.

This non-solvated crystalline form is particularly preferred for use in the manufacture of pharmaceutical compositions.

Example 1

Preparation of Amorphous Form

The amorphous material of the instant invention was prepared by dissolving 5 g of crystalline raloxifene hydrochloride in 300 ml of methanol and 22.5 ml of water. The amorphous material was recovered by spray drying the solution using a Buchi Model 190 Mini spray dryer under the following conditions: equilibrium inlet temperature: 84° C.; equilibrium outlet temperature: 60° C.; approx. spray rate: 2.5 ml/min.; aspirator setting: 20; air flow indicator: 500–600; atomization pressure: 35 psi. The process was completed in 2 hours and 10 minutes.

The material recovered after spray drying was observed under a polarized light microscope to determine if the product was birefringent. No birefringence was observed, and the material was considered to be amorphous.

Table 4 provides comparative solubility data in water between the crystalline and amorphous material:

TABLE 4

| Form | Solubility (mg/ml) | Temp., ° C. |
|---|---|---|
| crystalline | 0.08 | room temperature |
| amorphous | 42.2 | room temperature |
| amorphous | 120 | 37° C.* |

*in sonicator

The amorphous material was also made as a complex with povidone, with ratios of raloxifene HCl to PVP as follows: 9:1, 3:1, and 1:1 (w/w). Complexes with hydroxypropyl-β-cyclodextrin (HPBCD) were also prepared, with a ratio of raloxifene HCl to HPBCD of from 1:1 to 1:4 (w/w). These were added to increase solubility and to prevent any potential crystallization of the material, for example, which may or may not occur when a supersaturated solution was prepared from the amorphous form. Some lots were recovered as crystalline material, or the material was converted to a crystalline form within about a week or 10 days after preparation. The lots recovered as amorphous material which did not crystallize within about 10 days were observed to remain amorphous.

Example 2

Bioavailability Study

The extent and rate of absorption of the crystalline and amorphous forms of raloxifene HCl was determined. The two forms of the compound were formulated in a PEG vehicle as follows:

| Component | % by weight |
|---|---|
| Polyethylene glycol 1450 | 70 |
| spray dried lactose | 1.5 |
| colloidal silicon dioxide | 1.5 |
| polysorbate 80 | 2.0 |
| raloxifene HCl | 25 |

Figure 1:
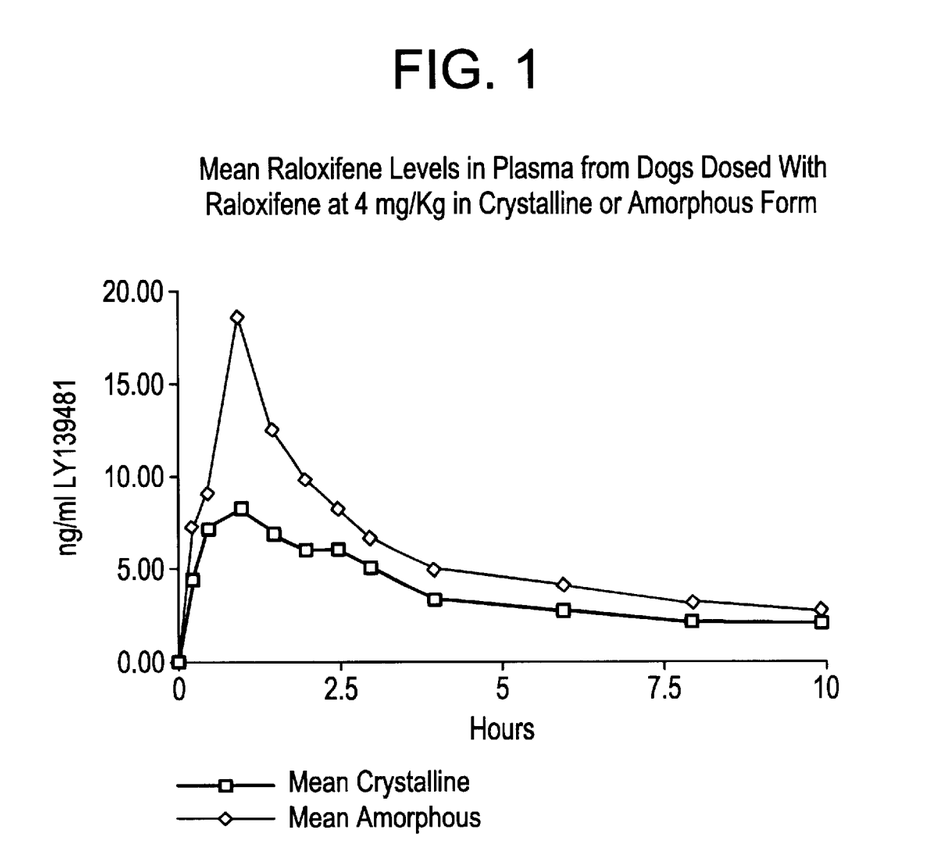
FIG. 1 illustrates the mean raloxifene levels in plasma from dogs treated with either crystalline or amorphous forms of a compound of formula I.

Six dogs were dosed as follows: three dogs received the amorphous form, while three dogs received the crystalline form, both at a dose of 4 mg/kg. Plasma levels of the two compound forms were then determined over a 10 hour period. The results from this study are provided in FIG. 1. This study indicated greater bioavailability with the amorphous form.

The following discussions illustrate methods of use for the compounds of formula I in experimental models or in clinical studies. These examples are for the purposes of illustration and are not meant to be limiting in any way.

A. Osteoporosis:

Experimental models of postmenopausal osteoporosis are known in the art. Germane to this invention is the ovariectomized rat model which is provided in U.S. Pat. No. 5,393,763. The compounds of formula I would be active in this model and would demonstrate an effective treatment or prevention of bone loss due to the deprivation of estrogen.

An additional demonstration of the method of treating or preventing osteoporosis due to estrogen deprivation would be as follows: One hundred patients would be chosen, who are healthy postmenopausal women, aged 45–60 and who would normally be considered candidates for estrogen replacement therapy. This includes women with an intact uterus, who have had a last menstrual period more than six months, but less than six years. Patients excluded for the study would be those who have taken estrogens, progestins, or corticosteroids six months prior to the study or who have ever taken bis-phosphonates.

Fifty women (test group) would receive 15–80 mg of a compound of formula I, for example, Formulation 1 (above), per day. The other fifty women (control group) would receive a matched placebo per day. Both groups would receive calcium carbonate tablets (648 mg) per day. The study is a double-blind design. Neither the investigators nor the patients would know to which group each patient is assigned.

A baseline examination of each patient includes quantitative measurement of urinary calcium, creatinine, hydroxyproline, and pyridinoline crosslinks. Blood samples are measured for serum levels of osteocalcin and bone-specific alkaline phosphatase. Baseline measurements would also include a uterine examination and bone mineral density determination by photon absorptiometry.

The study would continue for six months, and each of the patients would be examined for changes in the above parameters. During the course of treatment, the patients in the treatment group would show a decreased change in the biochemical markers of bone resorption as compared to the control group. Also, the treatment group would show little or no decrease in bone mineral density compared to the control group. Both groups would have similar uterine histology, indicating the compounds of formula I have little or no utrotrophic effects.

B. Hyperlipidemia:

Experimental models of postmenopausal hyperlipidemia are known in the art. Germane to this invention is the ovariectomized rat model which is detailed in U.S. Pat. No. 5,464,845. Estrogenicity may further be assessed by evaluating the response of eosinophil infiltration into the uterus. A demonstration of:the method of treating hyperlipidemia due to estrogen deprivation would be as follows: One hundred patients would be chosen, who are healthy postmenopausal women, aged 45–60, and who would normally be considered candidates for estrogen replacement therapy. This would include women with an intact uterus, who have not had a menstrual period for more than six months, but less than six years. Patients excluded for the study would be those who have taken estrogens, progestins, or corticosteroids.

Fifty women (test group) would receive 15–80 mg of a compound of formula I, for example, using Formulation 1, per day. The other fifty women (control group) would receive a matched placebo per day. The study would be a double-blind design. Neither the investigators nor the patients would know to which group each patient is assigned.

A baseline examination of each patient would include serum determination of cholesterol and tri-glyceride levels. At the end of the study period (six months), each patient would have their serum lipid profile taken. Analysis of the data would confirm a lowering of the serum lipids, for example, cholesterol and/or tri-glycerides, in the test group versus the control.

From the foregoing, it will be seen that this invention is one well adapted to attain all the ends hereinabove set forth together with advantages that are inherent to the invention. It will be understood that certain features and subcombinations are of utility and may be employed without reference to other features and subcombinations. This is contemplated by and within the scope of the claims. Because many possible embodiments can be made of the invention without departing from the scope thereof, it is to be understood that all matter herein set forth is to be interpreted as illustrative and not in a limiting sense.

We claim:

1. A hydrochloride salt or a compound of formula I wherein:

$R^1$ and $R^3$ are independently hydrogen;

$R^2$ is piperidinyl; or a pharmaceutically acceptable solvate thereof, in an amorphous form.

2. A compound according to claim 1 wherein $R^1$ and $R^3$ each are hydrogen, $R^2$ is piperidinyl, and the hydrochloride salt thereof.

3. A compound according to claim 1 which is 6-hydroxy-2-(4-hydroxyphenyl)-3-[4-(2-piperidinylethoxy)benzoyl]benzo[b]thiophene hydrochloride salt.

4. A process for preparing an amorphous form of a compound of claim 1 which comprises preparing a solution of a crystalline form of a compound of formula I in a suitable solvent, and then spray drying said solution to recover an amorphous form of a compound of formula I.

5. The process of claim 4 wherein said suitable solvent is a mixture of methanol and water.

6. The process of claim 4 wherein said spray drying is effected in the presence of an inert gas.

7. A pharmaceutical formulation comprising a compound according to claim 1 in combination with a pharmaceutically acceptable carrier, diluent, or excipient.

8. A method for the inhibition of bone loss or bone resorption which comprises administering to a patient in need thereof a compound according to claim 1.

9. The method according to claim 8 wherein said bone loss or bone resorption occurs as a result of menopause or ovariectomy.

10. A method of inhibiting serum cholesterol levels which comprises administering to a patient in need thereof a compound according to claim 1.

* * * * *